US008392342B2

(12) United States Patent
Mangione-Smith

(10) Patent No.: US 8,392,342 B2
(45) Date of Patent: Mar. 5, 2013

(54) METHOD AND APPARATUS FOR PREDICTING MOVEMENT OF A TOOL IN EACH OF FOUR DIMENSIONS AND GENERATING FEEDBACK DURING SURGICAL EVENTS USING A 4D VIRTUAL REAL-TIME SPACE

(75) Inventor: William H. Mangione-Smith, Kirkland, WA (US)

(73) Assignee: Empire Technology Development LLC, Wilmington, DE (US)

( * ) Notice: Subject to any disclaimer, the term of this patent is extended or adjusted under 35 U.S.C. 154(b) by 624 days.

(21) Appl. No.: 12/621,424

(22) Filed: Nov. 18, 2009

(65) Prior Publication Data
US 2011/0119224 A1     May 19, 2011

(51) Int. Cl.
*G06F 15/18*    (2006.01)
(52) U.S. Cl. ........................................... 706/12
(58) Field of Classification Search ............ 706/12, 706/45, 62
See application file for complete search history.

(56) References Cited

U.S. PATENT DOCUMENTS
2006/0149134 A1*   7/2006   Soper et al. .................. 600/182

OTHER PUBLICATIONS

Willoughby et al., Target Localization and Real Time Tracking Using THe Calypso 4D Localization System in PAtients With Localized Prostate Cancer, 2006, Elseviewer, pp. 528534.*
Mayer et al., A robotic system providing force feedback and automation for minimally invasive heart surgery, 2006, Int J CARS,Springer, pp. 1-3.*
Abolhassani et al., Minimization of needle deflection in robot assisted prostate barchytherapy, 2006, Springer, pp. 1-3.*
Rosen et al., The BlueDragon—A system for measuring the kinematics and the dynamics of minimally invasive surgical tools In-Vivo, 2002, IEEE, pp. 1-6.*
Holmes et al., 3D visualization, analysis, and treatment of the prostate using trans-urethral ultrasound, 2003, Elseviewer , pp. 1-11.*
GGoksel et al., 3D needle tissue interaction simulation for prostate bracytherapy, 2005. Springer-Verlag, pp. 1-8.*
Sgambelluri, et al. "An Artificial Neural Network approach for Haptic Discrimination in Minimally Invasive Surgery", Appearing in *Robot and Human interactive Communication*, Aug. 26-29, 2007. pp. 25-30.
Nakao, et al. "A Haptic Navigation System for Supporting Master-Slave Robotic Surgery", Appearing in *Int Conf Artif Real Telexistence*, vol. 13; pp. 209-214. 2003.
Okamura, et al. "Methods for haptic feedback in teleoperated robot-assisted surgery", Appearing in *Industrial Robot: An International Journal*, vol. 31, No. 6, 2004. pp. 499-508.

* cited by examiner

*Primary Examiner* — David Vincent
(74) *Attorney, Agent, or Firm* — Perkins Coie LLP

(57) ABSTRACT

Technology is disclosed for communicating surgical information. The technology can receive a first data from a first sensor coupled to a first tool; receive a second data from a second sensor coupled to a second tool; generate a virtual model of a virtual real-time space, wherein the first tool is mapped in the virtual real-time space in relation to a first vital entity and a second vital entity via the first sensor and based on the first data; apply the virtual real-time space against at least a first probabilistic model and a second probabilistic model to obtain a third data about movement of the first tool in relation to the first vital entity and the second vital entity; and output the third data to an output device to convey information about the first tool.

22 Claims, 6 Drawing Sheets

METHOD AND APPARATUS FOR PREDICTING MOVEMENT OF A TOOL IN EACH OF FOUR DIMENSIONS AND GENERATING FEEDBACK DURING SURGICAL EVENTS USING A 4D VIRTUAL REAL-TIME SPACE

BACKGROUND

Modern medicine sometimes employs surgical procedures ("surgery"), e.g., to remove, repair, or insert various organs, tissues, bone, or other "entities." These entities may be original, replacement (e.g., from a donor), or artificial; and life forms (e.g., humans, animals, or other creatures) may employ such entities in both routine and extraordinary efforts.

Highly educated and skilled professionals ("surgeons") generally perform surgery. Surgeons are accustomed to using several senses, including sight, hearing, touch, and sometimes even smell to guide their actions while in an operating room. Surgeons rarely rely on only one sense and more often augment a primary sense with other information or senses. Surgeons may also employ their senses to complement each other. As an example, touch can be used when manipulating a surgical tool ("instrument" or simply "tool") without a clear line of sight, e.g., to distinguish between various organs, bone, tissue, fluids, etc., when the instrument cannot be seen while it is inserted in a patient undergoing the surgery.

In some cases, surgeons may perform procedures remotely, such as by using remotely guided robotic surgical tools. In such cases, the surgeons may not be able to rely on all of the senses that they are accustomed to using when directly operating on a patient.

Surgeons sometimes mistakenly damage an entity unrelated to the surgery. As examples, the surgeon may mistakenly puncture a lung during heart surgery; damage a muscle during ligament surgery; etc. These mistakes can occur, for example, because of incorrect use of the surgical tools, unreliability of commonly used senses, inability to accurately position the surgical tools, etc.

DETAILED DESCRIPTION

Figure 1:
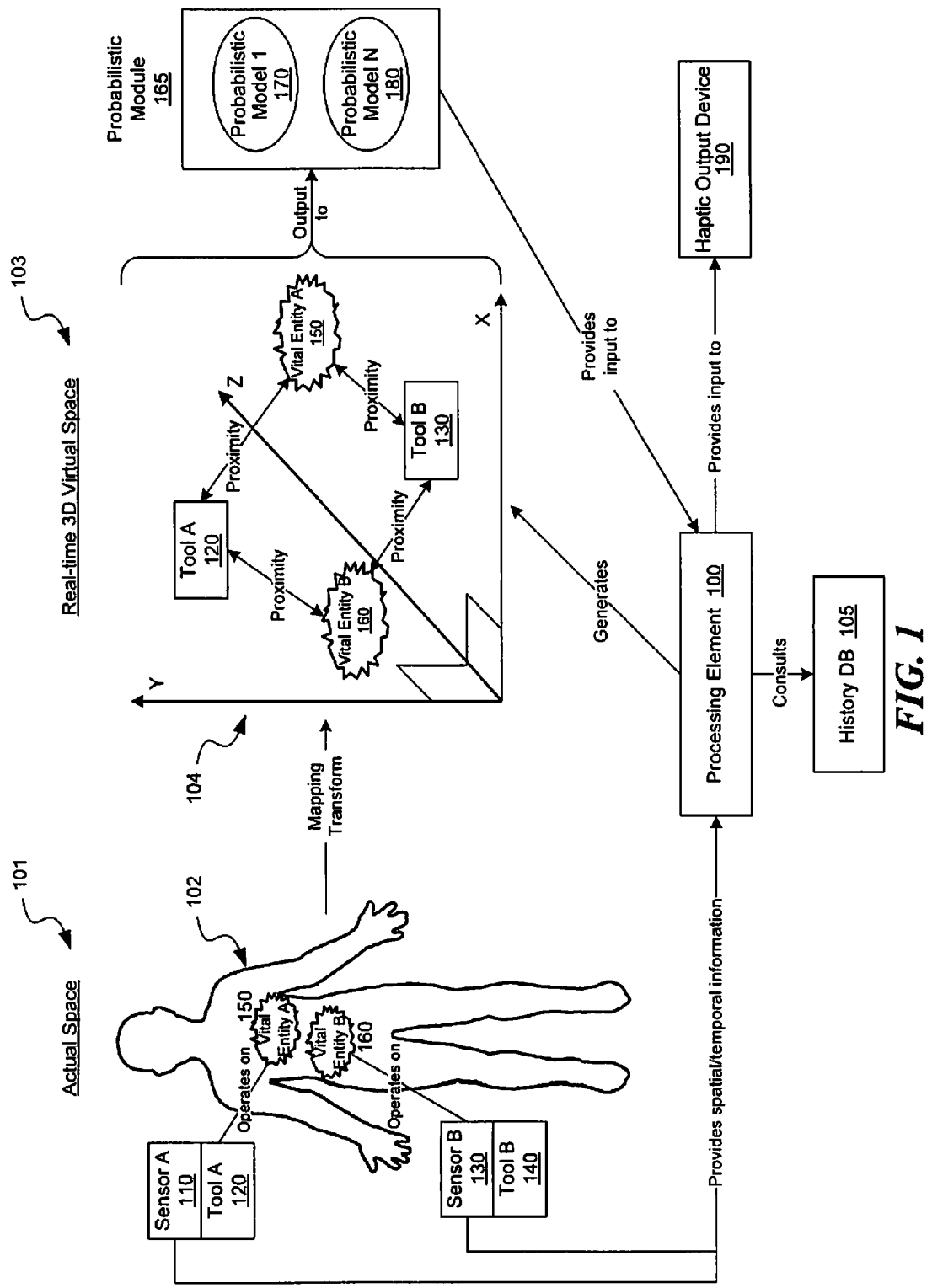
FIG. 1 is a schematic diagram illustrating feedback technology described herein in some embodiments.

Feedback technology is described for providing feedback during surgery that is based on the position of surgical tools and an analysis of probabilistic models developed through historical analysis. In various embodiments, the feedback technology monitors the position of surgical tools during surgical procedures, receives information on outcome (e.g., success or failure), and updates a probabilistic model based on the historical positions and movements of the tool ("historical information") and the outcome information. The feedback technology can also provide feedback during surgery indicative of a predicted outcome. The feedback can be received via various senses, such as haptic (e.g., pressure, vibration, temperature, etc.), audible, visual, smell, etc.

The feedback technology receives information, e.g., surgical tool position and/or movement information, during surgical procedures. In various embodiments, the feedback technology can monitor the position or movement of surgical tools using general-purpose cameras (e.g., digital cameras or video cameras); special-purpose cameras (e.g., infrared cameras); radiofrequency identification (RFID) tags or devices attached to surgical tools ("tools"), and associated monitoring equipment; or other means. The feedback technology can also detect the position of entities (e.g., vital entities, such as the heart, lungs, kidneys, etc.). The feedback technology can then employ a mapping transformation to transform the received position and/or movement information of the surgical tools and the received position information of the entities to create a three-dimensional model (e.g., in real-time). As the surgeon performs the surgery ("operates") using the surgical tools, the feedback technology can employ probabilistic models, e.g., to predict various outcomes. As an example, the feedback technology may determine that a surgical tool is likely to penetrate a vital entity that is not part of the surgical procedure. In such a case, the feedback technology may provide various forms of feedback, such as vibrations, sounds, lights, smells, heat, etc.

In various embodiments, devices can be coupled to surgical tools to enable detection of position and movement. As examples, transponders, RFID tags, sensors, cameras, microphones, or other devices may be coupled to surgical tools. These devices may transmit or otherwise enable detection of position factors. Example of position factors are speed, orientation, acceleration, etc.

One or more detectors may detect and store the position factors, e.g., at a specified periodicity or when changes in the position factors are detected. In various embodiments, the detectors can be object recognition and tracking tools that can employ cameras to locate the surgical tools in three dimensions. Infrared ("IR") cameras can augment this capability by distinguishing biological materials from tools. Magnetic resonance imaging, x-ray, ultrasound, or other imaging technologies can also be employed to detect the position factors. In some embodiments, the feedback system can employ RFID detectors to detect tool position. The feedback technology can store the detected position factors in a database.

The feedback technology can generate one or more virtual three dimensional (3-D) models of the surgical area based on the stored position factors, events, or other information (collectively, "stored data") stored during the surgery. The feedback technology can also determine motion history of the surgeon's hands and tools, based on the stored data. The feedback technology can update this 3-D model in real-time based on the data it detects and stores. Thus, the virtual models can be considered to be virtual real-time spaces because they are updated during surgery. A virtual real-time space can include dimensions along various dimensions or axes (e.g., length, width, and height). In some embodiments, the feedback technology can employ a fourth dimension, e.g., time, to create a four-dimensional (4-D) model. In various embodiments, the feedback technology may translate the 3-D model into a mesh representation of the surface using finite element approaches from computer assisted design ("CAD") and other physical modeling techniques.

During the surgery, the surgeon or some other operator may additionally indicate various events that can also be stored. As examples, the operator can indicate whether or not aspects of the surgical procedure were successful, whether or not an entity that was not to have been disturbed during surgery was nevertheless adversely affected, etc. In various embodiments, these events may be detected automatically. As an example, cameras, electromechanical devices, optoelectric devices, or other devices may detect that an entity was disturbed or even damaged.

In various embodiments, the feedback technology can apply probabilistic models using the stored data to predict the movement of the tools, and then forward the predicted information as feedback to the surgeon. As an example, the feedback technology can provide feedback via haptic devices, e.g. gloves that the surgeon may employ during the surgery. These haptic devices can provide the feedback to the surgeon (or others) based on how the tools are moving or predicted to move in relation to entities. Examples of feedback are temperature, vibration, sound, heat, etc. When the surgical tool is predicted to come too close to a vital entity that is not being operated upon, it may increase the temperature, begin vibrating, emanate sounds, etc. As a result, the surgeon can develop a better feel for how the tool should or should not be used.

In some embodiments, motion history of the surgical tools can be obtained by using the cameras, RFID and related real-time tracking technology discussed above. The motion history can then be incorporated with the 3-D model to produce an augmented model that includes information on both where the surgical tool is and where it was, along with other useful information such as velocity and acceleration.

The feedback technology can track multiple models and assign weights to the models according to reliability to produce a hazard warning score or signal. The feedback technology can communicate this hazard warning score to the surgeon, e.g., using sound pitch, temperature, vibration frequency, etc. As an example, a high hazard warning score may be associated with a higher sound pitch, temperature, or vibration frequency than a lower hazard warning score.

In some embodiments, the feedback technology can be configured as follows: model 1 models a risk of puncturing the left lung; model 2 models a risk of slicing the liver; model 3 models a risk of electrocuting the heart. The feedback technology can track history over time. As an example, the feedback technology can determine if one of the models indicates rapidly increasing risk. The feedback technology can track reliability over a longer period of time. The feedback technology can adjust the hazard warning score based on this reliability. As an example, the feedback technology may determine that a well established lung model has better reliability than a less established heart model that has not yet been validated. The feedback technology may also adjust the indicated reliability (and consequently the hazard warning score) based on one or more external conditions. As an example, because a particular life form (e.g., human) has two lungs but only one heart, the feedback technology may adjust the reliance on the models to account for the significant additional risk of damaging the heart.

In some embodiments, the feedback technology may communicate an audible warning, e.g., by playing a sound and varying its volume, pitch, or pattern to indicate different hazard warning scores. Alternatively, the feedback technology may employ a synthetic voice, e.g., to speak "warning— high probability of injuring the heart". In various embodiments, the feedback technology may employ other means of communicating warnings, such as by stimulating the surgeon's hands, feet, or other parts of the body via output devices, e.g., to provide feedback to the surgeon via a tickle or a pinch. In various embodiments, the feedback technology can employ more than one of such output devices simultaneously. As an example, the output device may increase a sound pitch as the hazard warning score increases, and then increase the temperature of a patch applied to the surgeon's back if the patient's lung is near collapse. The feedback system can employ various gratification units as feedback. A gratification unit is a level of feedback that is discernable from another level. For example, two different frequencies of vibration that a surgeon can perceive as different may be associated with different hazard warning scores. Gratification units can be emitted as discrete (e.g., synthetic voice) or continuous (e.g., temperature) output.

The feedback technology can include: sensors, a processing system, and one or more feedback output devices. The sensors can include auditory, ultrasound, visual, capacitive, or others. These sensors can be mounted on surgical tools, manipulative arms (either mechanical or human), in the surgical area (e.g. on vital entities), etc. Sensors on surgical tools can be mounted with glue, screws, epoxy, tape, welding, or though a combined physical housing or mounting construct, such as a camera carrying unit with an adjustable clamp. Fiducials can be placed at various regions, e.g., a paper tag on a liver or RFID tags on the kidney, to identify regions where entities or hazards exist. Thermometers can be placed in the life form to detect temperature. A surgical camera can be placed within a cavity of the life form to improve viewing angle. The processing component can include signal processing capabilities and can be collocated or remotely located from any of the other components. The feedback output device can include haptic devices to be worn by the surgeon, speakers, lights, patches to be applied to the surgeon's body, etc.

The numerous advantages of the feedback technology will be readily apparent to one skilled in the art. For example, using the feedback technology, a surgeon can track how close a scalpel is to the lung because the feedback technology can produce a warning when the scalpel approaches to within less than 2 cm feedback technology of the lung and increase the warning level as it gets closer. The feedback technology can produce similar warnings when a syringe approaches too close to the heart. The warnings can take into account the velocity of the surgical tool. As an example, when it is 1 cm from the heart but moving away, a lower warning level can be indicated than when it is 1 cm and rapidly moving towards the heart.

The technology will now be described with reference to the Figures ("drawings"). In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

FIG. 1 is a schematic diagram illustrating the feedback technology described herein in some embodiments. The feedback technology can include an actual space 101 and a real-time 3-D virtual space 103. Actual space 101 can include a patient 102 on whom a surgeon (not illustrated) is operating. Patient 102 may have one or more entities, such as a first vital entity 150 (e.g., a heart) and a second vital entity 160 (e.g., a kidney). As a surgeon operates using a first surgical tool 120 and/or a second surgical tool 140, sensors associated with the tools may enable detection of position factors, e.g., position, speed, rotation, acceleration, angle, etc. As an example, a first sensor 110 associated with first surgical tool 120 and a second sensor 130 associated with second surgical tool 140 may enable detection of the position factors. In various embodiments, the sensors may actively transmit the position factors or passively respond to the detectors. A processing element 100 can employ the detected position factors along with a database 105 of historical information (e.g., position factors and success/failure information) to generate real-time 3-D virtual space 103 and to provide feedback via an output device, e.g., via a haptic output device 190. Real-time 3-D virtual space 103 can be a logical or mathematical transformative representation 104 of actual space 101. As an example, the processing element 100 may transform physical data received from the sensors and other input devices (e.g., cameras) into real-time 3-D virtual space 103. Mathematical transformative representation 104 can map positions of the surgical tools (e.g., based on detected position factors) in relation to entities of patient 102 (e.g., based on position information detected from RFID or other tags, imaging apparatuses, etc.). A probabilistic module 165 can generate and/or update one or more probabilistic models, e.g., a probabilistic model 170 and a probabilistic model 180, based on mapped real-time 3-D virtual space 103. Processing element 100 can employ the probabilistic models to predict the future movement of the surgical tools and modify feedback provided by output device 190. As an example, if a model predicts that one of the vital entities will be damaged based on the predicted motion of a surgical tool, the processing element may change the pitch of a sound, increase a temperature, increase vibration, etc. In various embodiments, the processing element may vary the output provided by the output device by varying a voltage supply provided to the output device.

Figure 2:
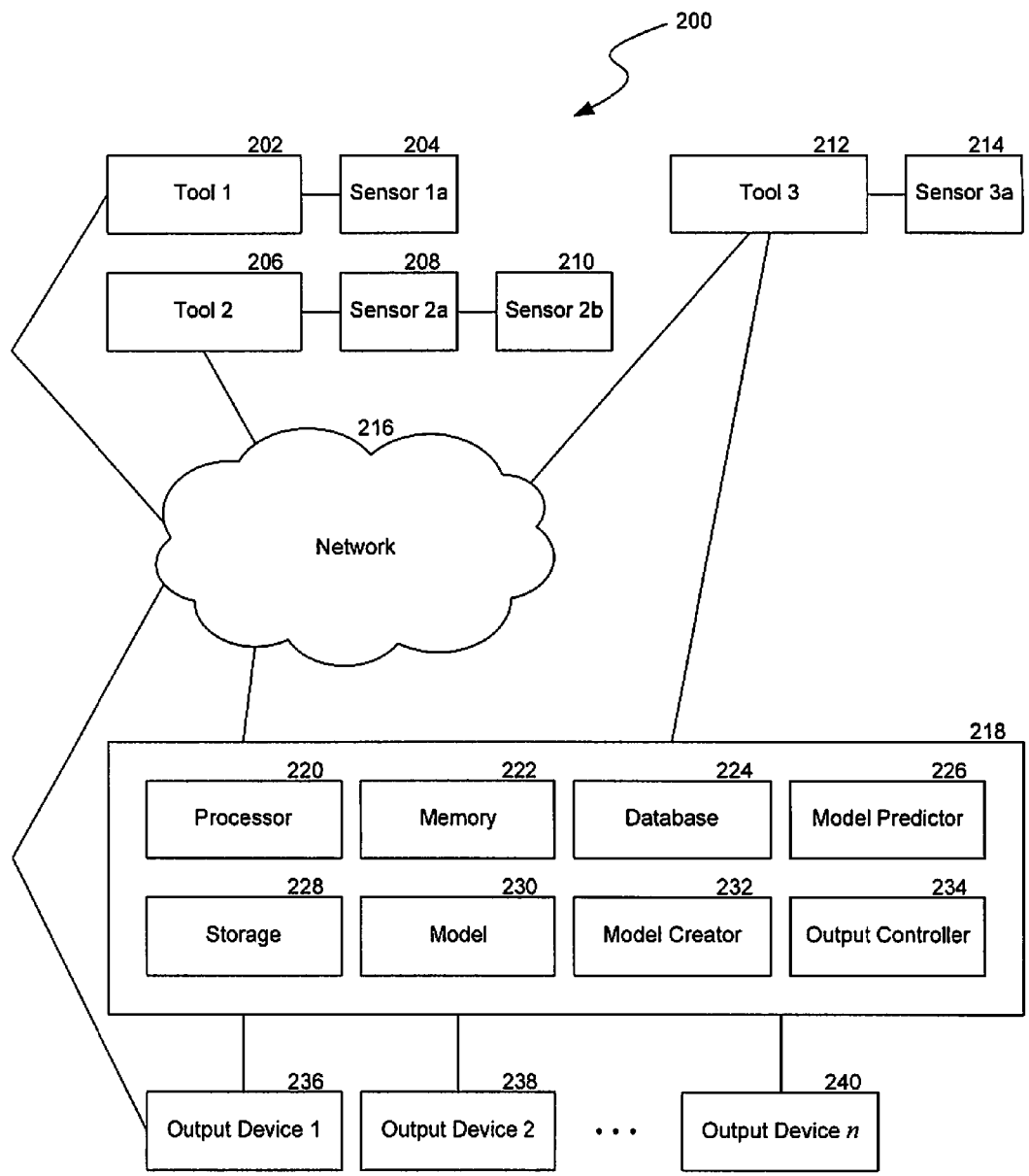
FIG. 2 is a block diagram illustrating an environment in which the feedback technology may operate in some embodiments.

FIG. 2 is a block diagram illustrating an environment 200 in which the feedback technology may operate in some embodiments. Environment 200 can include multiple tools, e.g., a surgical tool 1 202, a surgical tool 2 206, and a surgical tool 3 212. The surgical tools can be associated with one or more sensors. For example, surgical tool 1 202 is associated with a sensor 1a 204; surgical tool 206 is associated with sensors 2a 208 and 2b 210; and surgical tool 3 212 is associated with a sensor 3a 214. The surgical tools may be connected to a computing device 218 (e.g., a processing element 100 illustrated above in FIG. 1) directly and/or via a network 216. As examples, surgical tools 1 202 and 2 206 are connected via a network 216 to computing device 218; and surgical tool 3 212 is connected to computing device 218 both via network 216 and directly.

Computing device 218 can include several components, such as a processor 220, a memory 222, a database 224, a model predictor 226, a storage 228, a model 230, a model creator 232, and an output controller 234. Processor 220 can be a conventional or a special-purpose processor, such as a central processing unit. Memory 222 can be volatile or non-volatile memory. Database 224 can include one or more tables or databases, e.g., to store models (e.g. model 230), historical data, or other information. Model predictor 226 can predict tool motion based on stored models and/or historical data. Storage 228 can be disk or other storage (e.g., attached to or remote from the computing device) and may store an operating system, databases (e.g., database 224), etc. Model creator 232 may create one or more models 230 from historical data stored in database 224 or elsewhere, and may also update the model in real-time as additional data is received from sensors or other input and/or stored. Output controller 234 may control one or more output devices, e.g., output device 1 236, output device 2 238, and output device n 240, e.g. by varying voltage. Computing device 218 may be connected to output devices directly or via network 216. The output devices can provide various types of output, e.g., sounds, lights, vibration, heat, surface modification (e.g., smooth, rough, liquid, viscous, etc.), sensation (e.g., pinch), etc.

Figure 3:
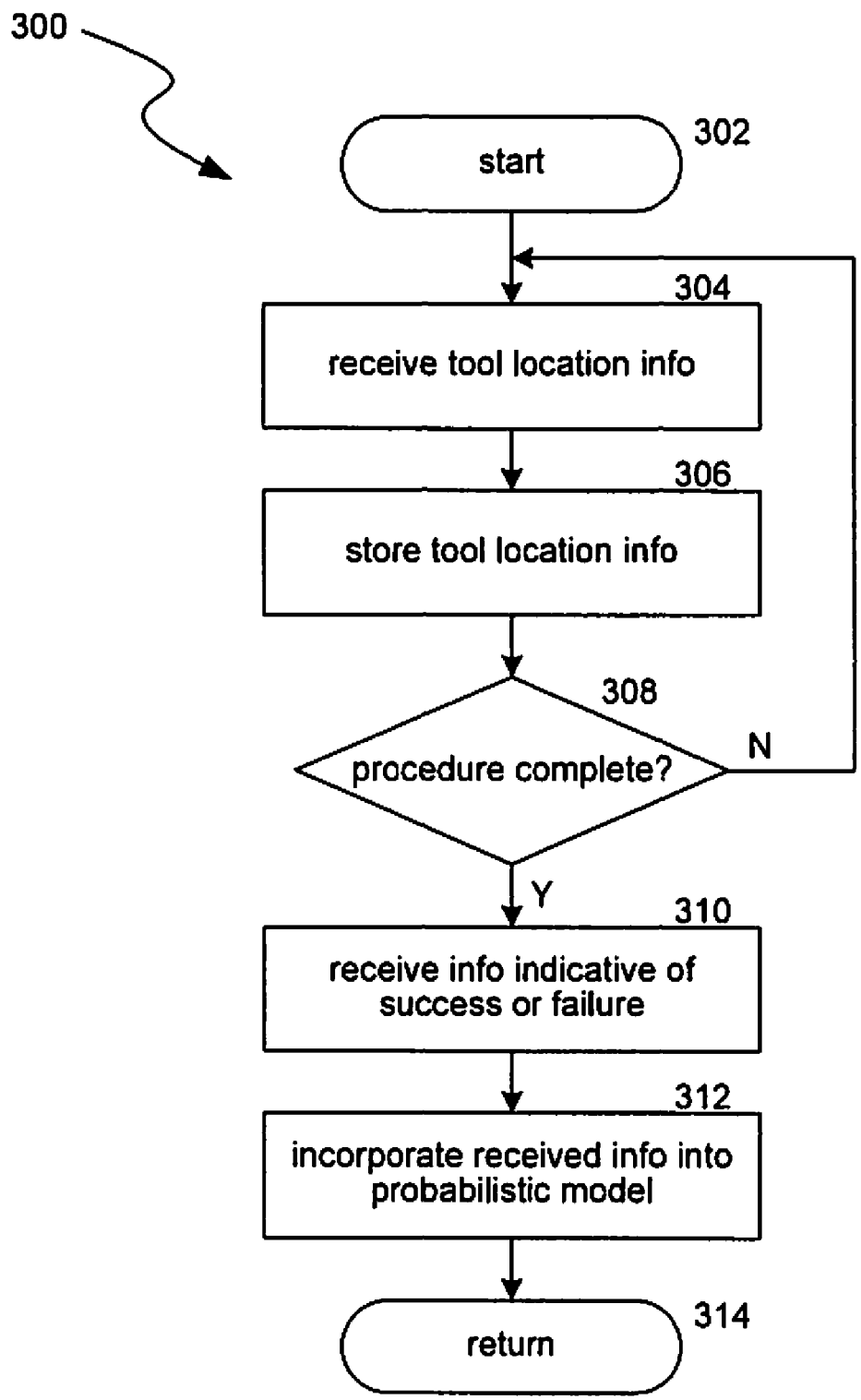
FIG. 3 is a flow diagram illustrating a routine invoked by the feedback technology in some embodiments to update a probabilistic model.

FIG. 3 is a flow diagram illustrating a routine 300 invoked by the feedback technology in some embodiments to update a probabilistic model. Routine 300 begins at block 302. Routine 300 may begin before, when, or after a surgical procedure is started. At block 304, the routine receives location factors, such as the location of a surgical tool, its speed, acceleration, rotation, angle, etc. At block 306, the routine stores the received information, e.g. in a database. The stored information may be incorporated into a probabilistic model. At decision block 308, the routine determines whether the surgical procedure is complete. As an example, a surgeon or an assistant may indicate that the surgical procedure is complete. In some embodiments, the surgical procedure may be indicated to be complete when a specified portion of the surgery is complete. If the surgical procedure is complete, the routine continues at block 310. Otherwise, the routine continues at block 304. At block 310, the routine receives information indicative of a success or failure of the surgical procedure. As an example, the surgeon or the assistant may indicate that the surgical procedure was completed successfully. At block 312, the routine incorporates the received information (e.g., success or failure) into a probabilistic model. At block 314, the routine returns.

Figure 4:
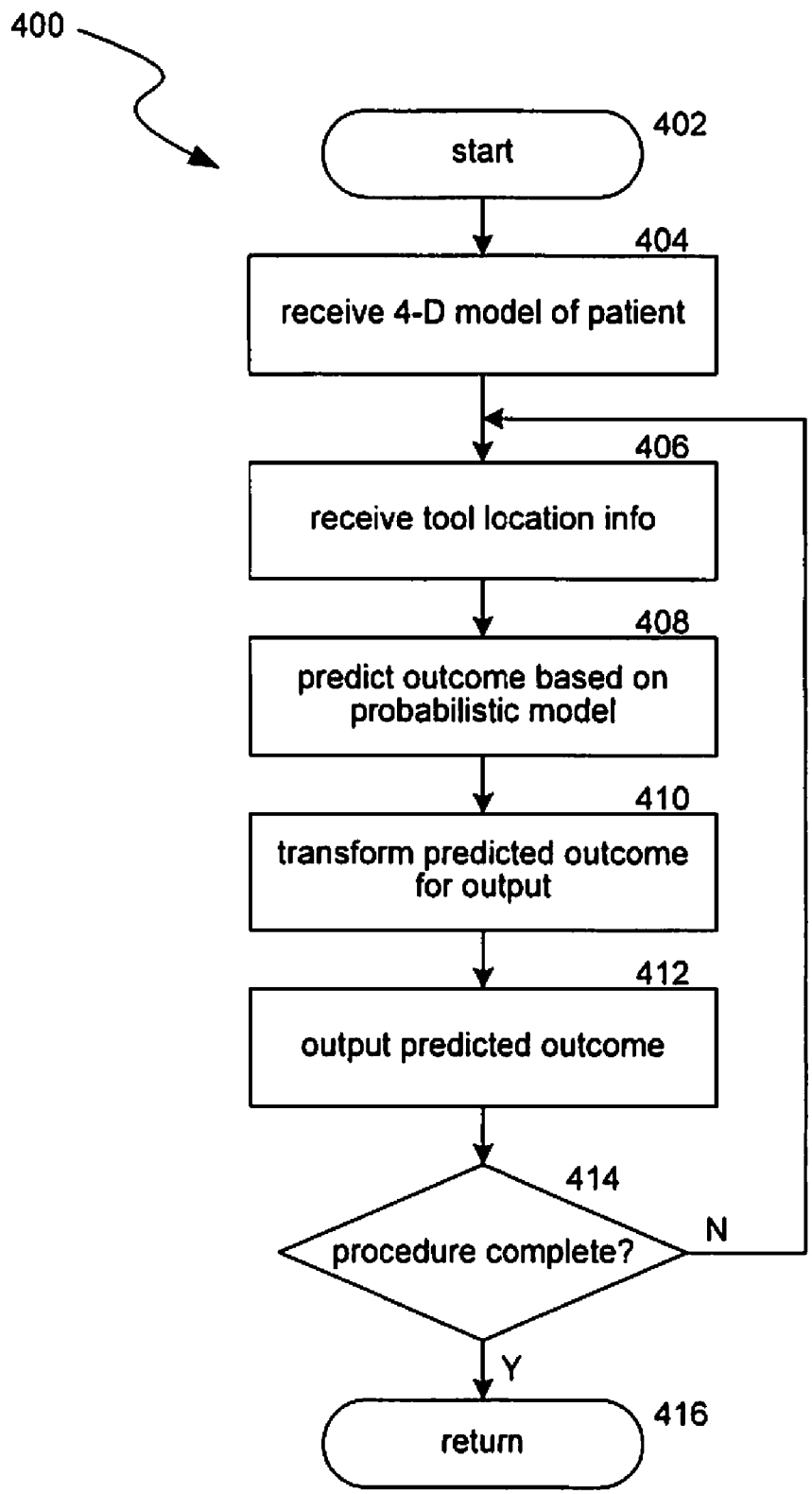
FIG. 4 is a flow diagram illustrating a routine invoked by the feedback technology to provide feedback during a surgical procedure in some embodiments.

FIG. 4 is a flow diagram illustrating a routine 400 invoked by the feedback technology to provide feedback during a surgical procedure in some embodiments. Routine 400 begins at block 402. At block 404, the routine receives a model, e.g., a virtual model of an operating area. As examples, the routine may receive a 4-D model or a 3-D model. At block 406, the routine receives information on the location of one or more surgical tools. At block 408, the routine predicts an outcome based on a probabilistic model. As examples, the routine may determine whether the surgical procedure will be successful (e.g., predict an outcome) based on the model and the current position factors of the tool. At block 410, the routine transforms the predicted outcome for output via an output device. As examples, the routine may transform the predicted outcome for output as vibrations, sounds, lights, heat, etc. At decision block 414, the routine determines whether the surgical procedure is complete. As an example, the routine may receive an indication from a surgeon or an assistant that the surgical procedure is complete. In some embodiments, the routine may determine that the surgical procedure is complete using other means, such as by observing whether the patient is undergoing a final suture. If the surgical procedure is complete, the routine continues at block 416, where it returns. Otherwise, the routine continues at block 406.

Those skilled in the art will appreciate that the logic shown in FIG. 4 and in each of the flow diagrams discussed below may be altered in a variety of ways. For example, the order of the logic may be rearranged; substeps may be performed in parallel; shown logic may be omitted, or other logic may be included; etc. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 5:
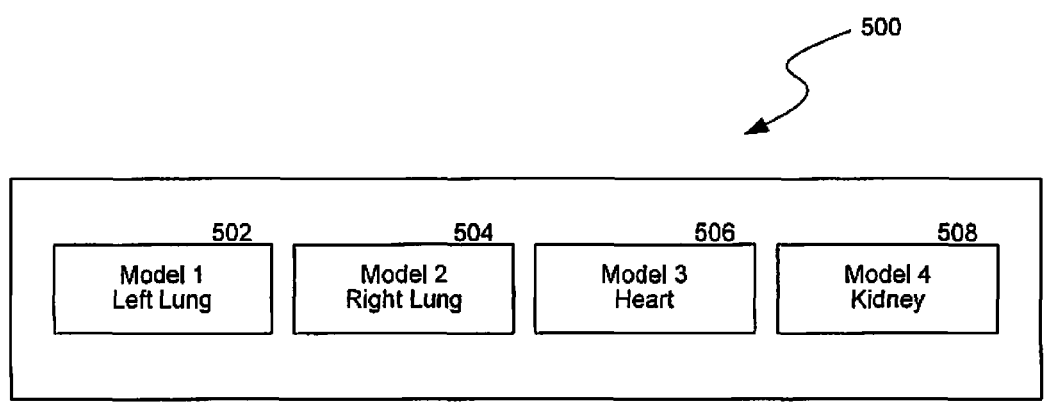
FIG. 5 is a block diagram illustrating probabilistic models in some embodiments.

FIG. 5 is a block diagram illustrating probabilistic models 500 in some embodiments. As depicted, probabilistic models 500 includes a first model of a left lung 502; a second model of a right lung 504; a third model of a heart 506; and a fourth model of a kidney 508. Only four probabilistic models are shown in probabilistic models 500 for simplicity, and one skilled in the art will appreciate that there may be a different number of probabilistic models in probabilistic models 500. The models can be stored as data in a database. Each model may be associated with a weight (not illustrated) indicative of reliability.

Figure 6:
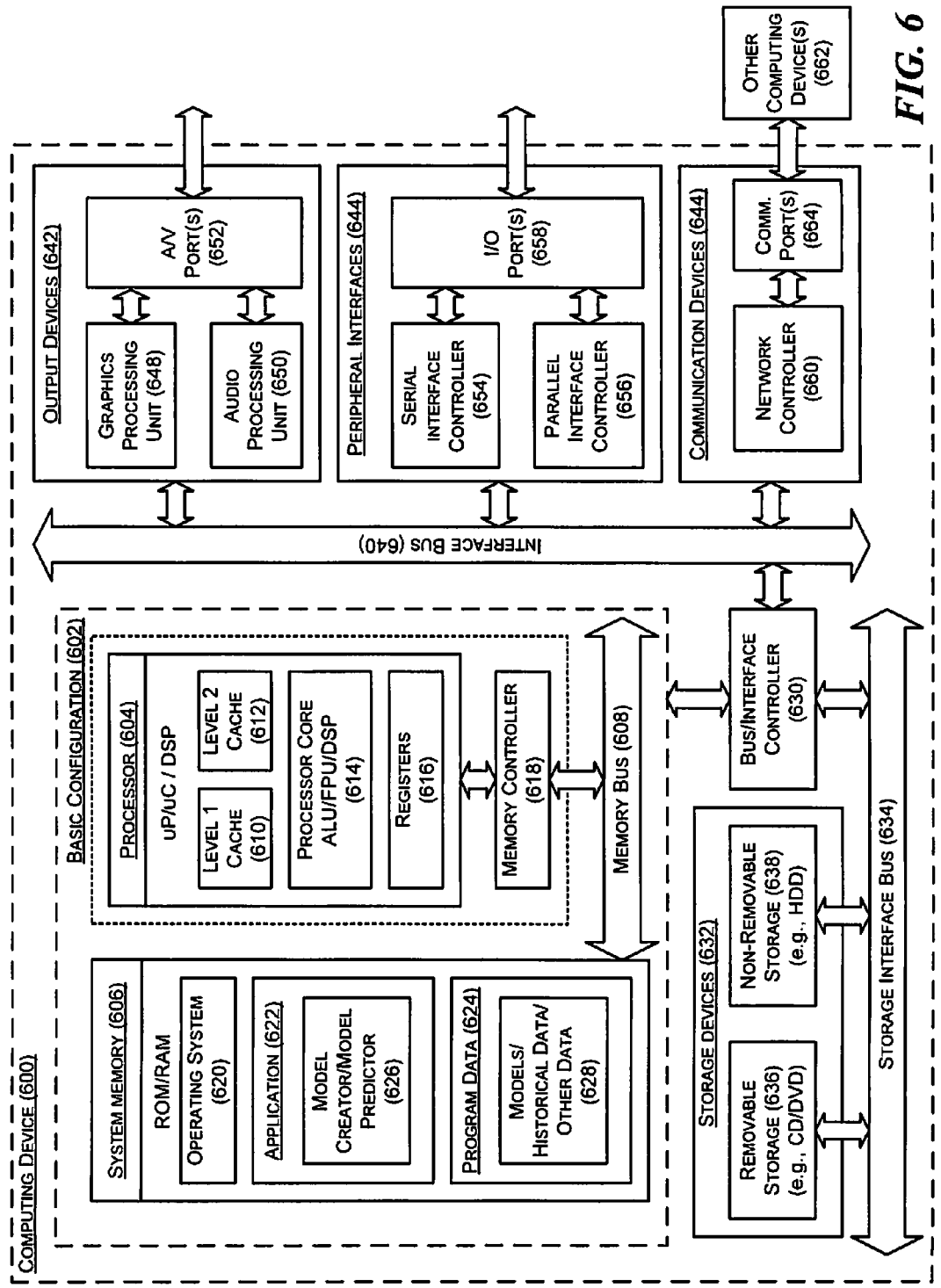
FIG. 6 is a block diagram illustrating an example of a computing device that can be arranged as a suitable computing system for use with the feedback technology in accordance with the present disclosure.

FIG. 6 is a block diagram illustrating an example of a computing device that can be arranged as a suitable computing system for use with the feedback technology in accordance with the present disclosure. In a very basic configuration 602, computing device 600 typically includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include one or more software components (e.g., a Model Creator/Model Predictor 626) that are arranged to generate and maintain models, predict surgical tool movement, compute hazard levels, etc. Software components 626 may employ hardware devices, such as detectors and feedback output devices. Program data 624 may include models/historical/other data 628 that may be useful for generating and maintaining models, and predicting motion of surgical tools. In some embodiments, application 622 may be arranged to operate with program data 624 on operating system 620. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, systems, or other specific examples or embodiments disclosed herein. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

I claim:

1. A method for communicating surgical information, comprising:
   receiving a first data from a first sensor coupled to a first tool;
   receiving a second data from a second sensor coupled to a second tool;
   generating a virtual model of a four-dimensional virtual real-time space, wherein the first tool is mapped in the virtual real-time space in relation to a first vital entity and a second vital entity via the first sensor and based on the first data;
   applying a first probabilistic model and a second probabilistic model within the four-dimensional virtual real-time space to obtain a third data comprising a prediction of movement of the first tool in each of the four dimensions in relation to the first vital entity and the second vital entity and a prediction score, wherein the prediction score indicates either a severity of a warning or an estimated reliability of the prediction of movement; and
   outputting the third data to an output device to convey information about the first tool.

2. The method of claim 1, wherein the applying includes accessing historical information from a data store to predict movement of the first tool.

3. The method of claim 1, wherein the third data further comprises a hazard warning signal.

4. The method of claim 3, wherein the hazard warning signal comprises at least one of a temperature signal, a vibration frequency, or a sound pitch.

5. The method of claim 1, wherein the first sensor is configured to measure auditory information, ultrasound, or visual information.

6. The method of claim 1, wherein the four-dimensional virtual model includes a length dimension, a width dimension, a height dimension, and a time dimension.

7. The method of claim 1, wherein the second tool is mapped in the four-dimensional virtual real-time space in relation to the first vital entity and the second vital entity via the second sensor and based on the second data.

8. The method of claim 7, further comprising:
   applying at least the first probabilistic model and the second probabilistic model within the four-dimensional virtual real-time space to obtain a fourth data about movement of the second tool in relation to the first vital entity and the second vital entity; and
   outputting the fourth data to the output device to convey haptic information about the second tool.

9. A non-transitory computer-readable storage medium storing computer-readable instructions that, when executed, perform a method comprising:
   receiving a first data from a first sensor coupled to a first tool;
   receiving a second data from a second sensor coupled to a second tool;
   generating a four-dimensional virtual model of a virtual real-time space, wherein the first tool is mapped in the four-dimensional virtual real-time space in relation to a first vital entity and a second vital entity via the first sensor and based on the first data;

applying at least a first probabilistic model and a second probabilistic model within the four-dimensional virtual real-time space to obtain a third data comprising a prediction of movement of the first tool in each of the four dimensions in relation to the first vital entity and the second vital entity; and outputting the third data to an output device to convey information about the first tool.

10. The non-transitory computer-readable storage medium of claim 9, wherein the applying includes accessing historical information from a data store to predict movement of the first tool.

11. The non-transitory computer-readable storage medium of claim 9, wherein the third data further comprises a hazard warning signal.

12. The non-transitory computer-readable storage medium of claim 11, wherein the hazard warning signal comprises at least one of a temperature signal, a vibration frequency, or a sound pitch.

13. The non-transitory computer-readable storage medium of claim 9, wherein the first sensor is configured to measure auditory information, ultrasound, or visual information.

14. The non-transitory computer-readable storage medium of claim 9, wherein the four-dimensional virtual real-time space includes a length dimension, a width dimension, a height dimension, and a time dimension.

15. The non-transitory computer-readable storage medium of claim 9, wherein the second tool is mapped in the four dimensional virtual real-time space in relation to the first vital entity and the second vital entity via the second sensor and based on the second data.

16. The non-transitory computer-readable storage medium of claim 15, further comprising:

applying at least the first probabilistic model and the second probabilistic model within the four dimensional virtual real-time space to obtain a fourth data about movement of the second tool in relation to the first vital entity and the second vital entity; and outputting the fourth data to the output device to convey haptic information about the second tool.

17. A system for communicating surgical information, comprising:

a component configured to receive a first data from a first sensor coupled to a first tool;

a component configured to receive a second data from a second sensor coupled to a second tool;

a component configured to generate a virtual model of a four-dimensional virtual real-time space, wherein the first tool is mapped in the four-dimensional virtual real-time space in relation to a first vital entity and a second vital entity via the first sensor and based on the first data;

a component configured to apply at least a first probabilistic model and a second probabilistic model within the four-dimensional virtual real-time space to obtain a third data comprising a prediction of movement of the first tool in each of the four dimensions in relation to the first vital entity and the second vital entity; and a component configured to output the third data to an output device to convey information about the first tool.

18. The system of claim 17, wherein a historical information from a data store is accessed to predict movement of the first tool.

19. The system of claim 17, wherein the third data further comprises a hazard warning signal.

20. The system of claim 19, wherein the hazard warning signal comprises at least one of a temperature signal, a vibration frequency, or a sound pitch.

21. The system of claim 17, wherein the third data further comprises a prediction score, the prediction score indicating either a severity of a warning or an estimated reliability of the prediction of movement.

22. The non-transitory computer-readable storage medium of claim 9, wherein the third data further comprises a prediction score, the prediction score indicating either a severity of a warning or an estimated reliability of the prediction of movement.

* * * * *

UNITED STATES PATENT AND TRADEMARK OFFICE
CERTIFICATE OF CORRECTION

PATENT NO. : 8,392,342 B2
APPLICATION NO. : 12/621424
DATED : March 5, 2013
INVENTOR(S) : Mangione-Smith It is certified that error appears in the above-identified patent and that said Letters Patent is hereby corrected as shown below:

On the Title Page, in Item (56), under "OTHER PUBLICATIONS", in Column 1, Lines 1-3, delete "Willoughby et al., Target Localization and Real Time Tracking Using THe Calypso 4D Localization System in PAtients With Localized Prostate Cancer, 2006, Elseviewer, pp. 528534.*" and insert -- Willoughby et al., "Target Localization and Real Time Tracking Using The Calypso 4D Localization System in Patients With Localized Prostate Cancer," 2006, Elseviewer, pp. 528-534.* --, therefor.

On the Title Page, in Item (56), under "OTHER PUBLICATIONS", in Column 2, Lines 1-3, delete "Mayer et al., A robotic system providing force feedback and automation for minimally invasive heart surgery, 2006, Int J CARS,Springer, pp. 1-3.*" and insert -- Mayer et al., "A robotic system providing force feedback and automation for minimally invasive heart surgery," 2006, Int. J. CARS., Springer, pp. 1-3.* --, therefor.

On the Title Page, in Item (56), under "OTHER PUBLICATIONS", in Column 2, Lines 4-5, delete "Abolhassani et al., Minimization of needle deflection in robot assisted prostate barchytherapy, 2006, Springer, pp. 1-3.*" and insert -- Abolhassani et al., "Minimization of needle deflection in robot assisted prostate brachytherapy," 2006, Springer, pp. 1-3.* --, therefor.

On the Title Page, in Item (56), under "OTHER PUBLICATIONS", in Column 2, Lines 6-8, delete "Rosen et al., The BlueDragon-A system for measuring the kinematics and the dynamics of minimally invasive surgical tools In-Vivo, 2002, IEEE, pp. 1-6.*" and insert -- Rosen et al., "The BlueDragon-A system for measuring the kinematics and the dynamics of minimally invasive surgical tools In-Vivo," 2002, IEEE, pp. 1-6.* --, therefor.

On the Title Page, in Item (56), under "OTHER PUBLICATIONS", in Column 2, Lines 9-10, delete "Holmes et al., 3D visualization, analysis, and treatment of the prostate using trans-urethral ultrasound, 2003, Elseviewer , pp. 1-11.*" and insert -- Holmes et al., "3D visualization, analysis, and treatment of the prostate using trans-urethral ultrasound,"

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,392,342 B2

2003, Elseviewer, pp. 1-11.* --, therefor.

On the Title Page, in Item (56), under "OTHER PUBLICATIONS", in Column 2, Lines 11-12, delete "GGoksel et al., 3D needle tissue interaction simulation for prostate bracytherapy, 2005. Springer-Verlag, pp. 1-8.*" and insert -- Goksel et al., "3D needle tissue interaction simulation for prostate brachytherapy," 2005, Springer-Verlag, pp. 1-8.* --, therefor.

On the Title Page, in Item (56), under "OTHER PUBLICATIONS", in Column 2, Lines 13-15, delete "Sgambelluri, et al. "An Artificial Neural Network approach for Haptic Discrimination in Minimally Invasive Surgery", Appearing in Robot and Human interactive Communication, Aug. 26-29, 2007." and insert -- Sgambelluri, et al., "An Artificial Neural Network approach for Haptic Discrimination in Minimally Invasive Surgery," Appearing in Robot and Human interactive Communication, Aug. 26-29, 2007, --, therefor.

On the Title Page, in Item (56), under "OTHER PUBLICATIONS", in Column 2, Lines 17-19, delete "Nakao, et al. "A Haptic Navigation System for Supporting Master-Slave Robotic Surgery", Appearing in Int Conf Artif Real Telexistence, vol. 13; pp. 209-214. 2003." and insert -- Nakao, et al., "A Haptic Navigation System for Supporting Master-Slave Robotic Surgery," Appearing in Int Conf Artif Real Telexistence, vol. 13, pp. 209-214, 2003. --, therefor.

On the Title Page, in Item (56), under "OTHER PUBLICATIONS", in Column 2, Lines 20-22, delete "Okamura, et al. "Methods for haptic feedback in teleoperated robot-assisted surgery", Appearing in Industrial Robot: An International Journal, vol. 31, No. 6, 2004. pp. 499-508." and insert -- Okamura, et al., "Methods for haptic feedback in teleoperated robot-assisted surgery," Appearing in Industrial Robot: An International Journal, vol. 31, No. 6, 2004, pp. 499-508. --, therefor.

In the Drawings:

In Fig. 6, Sheet 6 of 6, delete "uP/uC / DSP" and insert -- $\mu P/\mu C/DSP$ --, therefor.

In the Specification:

In Column 2, Line 16, delete "radiofrequency" and insert -- radio frequency --, therefor.

In Column 3, Line 17, delete "e.g." and insert -- e.g., --, therefor at each occurrence throughout the Specification.

In Column 8, Line 2, delete "(HDD)," and insert -- (HDDs), --, therefor.

In Column 8, Line 4, delete "(SSD)," and insert -- (SSDs), --, therefor.

In Column 8, Line 14, delete "(DVD)" and insert -- (DVDs) --, therefor.